(12) United States Patent
Parikh et al.

(10) Patent No.: US 12,042,491 B1
(45) Date of Patent: Jul. 23, 2024

(54) PHARMACEUTICAL FORMULATIONS OF QUINOLINES

(71) Applicant: TaP Pharmaceuticals, AG, Baar (CH)

(72) Inventors: Nilesh Parikh, Irvine, CA (US); William Hite, Winchester, CA (US)

(73) Assignee: TaP Pharmaceuticals AG, Zug (CH)

( * ) Notice: Subject to any disclaimer, the term of this patent is extended or adjusted under 35 U.S.C. 154(b) by 0 days.

(21) Appl. No.: 18/091,736

(22) Filed: Dec. 30, 2022

(51) Int. Cl.
| | |
|---|---|
| *A61K 31/4706* | (2006.01) |
| *A61K 9/00* | (2006.01) |
| *A61K 47/02* | (2006.01) |
| *A61K 47/10* | (2017.01) |
| *A61K 47/12* | (2006.01) |
| *A61K 47/18* | (2017.01) |

(52) U.S. Cl.
CPC ........ *A61K 31/4706* (2013.01); *A61K 9/0014* (2013.01); *A61K 47/02* (2013.01);
(Continued)

(58) Field of Classification Search
CPC .... A61P 3/10; A61P 35/00; A61P 3/04; A61P 43/00; A61P 25/28; A61P 25/00; A61P 19/02; A61P 9/10; A61P 25/16; A61P 29/00; A61P 25/18; A61P 3/00; A61P 31/00; A61P 35/02; A61P 35/04; A61P 9/12; A61P 15/00; A61P 21/00; A61P 9/00; A61P 25/08; A61P 25/14; A61P 25/22; A61P 25/24; A61P 31/12; A61P 1/04; A61P 17/00; A61P 37/02; A61P 17/06; A61P 11/00; A61P 19/10; A61P 37/06; A61P 11/06; A61P 13/12; A61P 1/00; A61P 37/08; A61P 31/22; A61P 27/02; A61P 1/16; A61P 31/04; A61P 31/18; A61P 19/08; A61P 19/04; A61P 17/02; A61P 37/00; A61P 19/00; A61P 1/02; A61P 17/04; A61P 7/00; A61P 31/14; A61P 25/02; A61P 21/04; A61P 3/14; A61P 15/16; A61P 11/08; A61P 11/02; A61P 13/02; A61P 27/16; A61P 7/06; A61P 25/04; A61P 33/00; A61P 27/14; A61P 31/20; A61P 3/06; A61P 9/04; A61P 31/16; A61P 33/06; A61P 15/08; A61P 9/14; A61P 13/10; A61P 1/18; A61P 13/08; A61P 19/06; A61P 7/02; A61P 23/00; A61P 17/14; A61P 25/20; A61P 15/10; A61P 5/14; A61P 27/06; A61P 31/10; A61P 39/00; A61P 11/14; A61P 13/00; A61P 17/10; A61P 27/00; A61P 33/14; A61P 41/00; A61P 5/16; A61P 1/08; A61P 15/04; A61P 15/18; A61P 17/16; A61P 27/12; A61P 3/08; A61P 5/34; A61P 7/04; A61P 21/02; A61P 25/06; A61P 37/04; A61P 5/38; A61P 1/12; A61P 1/14; A61P 11/10; A61P 15/02; A61P 17/08; A61P 25/36; A61P 29/02; A61P 31/06; A61P 31/08; A61P 33/02; A61P 33/04; A61P 33/10; A61P 33/12; A61P 39/02; A61P 5/00; A61P 5/40; A61P 9/08; A61P 7/10; A61P 9/06; A61P 1/10; A61P 11/04; A61P 11/16; A61P 25/30; A61P 25/32; A61P 3/02; A61P 33/08; A61P 5/18; A61P 5/24; A61P 5/48; A61P 5/50; A61P 7/08; A61K 45/06; A61K 31/5377; A61K 31/496; A61K 31/519; A61K 31/506; A61K 31/497; A61K 31/4545; A61K 2300/00; A61K 31/517; A61K 31/437; A61K 31/4709; A61K 31/495; A61K 31/5025; A61K 31/501; A61K 31/4985; A61K 9/0019; A61K 31/438; A61K 31/444; A61K 31/4406; A61K 31/52; A61K 31/44; A61K 31/47; A61K 38/1875; A61K 31/4745; A61K 9/0014; A61K 31/4965; A61K 31/541; A61K 31/55; A61K 39/39591; A61K 31/4706; A61K 31/4365; A61K 31/4439; A61K 31/505; A61K 31/513; A61K 38/00;
(Continued)

(56) References Cited

U.S. PATENT DOCUMENTS

| | | | | |
|---|---|---|---|---|
| 2013/0064815 | A1* | 3/2013 | Coller | A61K 45/06 |
| | | | | 424/133.1 |
| 2014/0088094 | A1* | 3/2014 | Glick | A61P 37/00 |
| | | | | 548/362.5 |
| 2021/0323925 | A1 | 10/2021 | Chen et al. | |

FOREIGN PATENT DOCUMENTS

| | | | | |
|---|---|---|---|---|
| CA | 3077089 | * | 10/2018 | ............... A61K 9/00 |
| CA | 3061185 | * | 11/2018 | ............... A61K 9/20 |

(Continued)

OTHER PUBLICATIONS

Heydari et al., "Simultaneous Determination of EDTA, Sorbic Acid, and Diclofenac Sodium in Pharmaceutical Preparations Using High-Performance Liquid Chromatography", AAPS PharmSciTech, vol. 14, No. 2, Jun. 2013, DOI: 10.1208/s12249-013-9962-0. (Year: 2013).*

(Continued)

*Primary Examiner* — Audrea B Coniglio

(57) ABSTRACT

Certain embodiments of the present disclosure provide liquid pharmaceutical formulations, suitable for oral administration, that contain from 10 mg/ml to 100 mg/ml of a cinchona alkaloid or a quinolone compound, e.g. chloroquine or hydroxychloroquine, a solvent that is at least one of a glycerin, a propylene glycol (PG), and a polyethylene glycol (PEG); and a carbonate. In such formulations, the solvent and the carbonate are present in amounts sufficient to promote resistance to hydrogen peroxide mediated degradation of the cinchona alkaloid or quinoline.

7 Claims, No Drawings

(52) U.S. Cl.
CPC .............. *A61K 47/10* (2013.01); *A61K 47/12* (2013.01); *A61K 47/183* (2013.01)

(58) Field of Classification Search
CPC .. A61K 36/81; A61K 2039/505; A61K 47/10; A61K 9/4858; A61K 31/551; A61K 9/0053; A61K 31/277; A61K 31/4355; A61K 31/185; A61K 31/397; A61K 31/4035; A61K 31/407; A61K 31/417; A61K 31/4184; A61K 31/435; A61K 31/451; A61K 31/5386; A61K 38/1793; A61K 9/4866; A61K 39/395; A61K 31/53; A61K 47/183; A61K 9/08; A61K 31/4375; A61K 31/498; A61K 38/1841; A61K 31/196; A61K 9/4816; A61K 9/4833; A61K 31/352; A61K 31/454; A61K 31/553; A61K 38/18; A61K 9/0024; A61K 9/14; A61K 31/4409; A61K 47/02; A61K 31/202; A61K 31/395; A61K 9/06; A61K 9/4825; A61K 31/455; A61K 31/635; A61K 31/452; A61K 31/46; A61K 48/00; A61K 2039/53; A61K 31/7115; A61K 31/715; A61K 47/12; A61K 47/22; A61K 31/192; A61K 31/40; A61K 9/0048; A61K 9/006; A61K 9/2095; A61K 2039/572; A61K 31/167; A61K 31/34; A61K 31/427; A61K 31/738; A61K 38/1709; A61K 38/39; A61K 39/3955; A61K 47/36; A61K 9/19; A61K 9/50; A61K 2039/55516; A61K 2039/10; A61K 31/137; A61K 31/255416; A61K 31/4172; A61K 31/567; A61K 31/57; A61K 31/7008; A61K 31/728; A61K 36/00; A61K 39/00; A61K 39/38; A61K 47/40; A61K 48/0075; A61K 8/31; A61K 9/2013; A61K 9/2054; A61K 2039/5156; A61K 2039/515835; A61K 31/353; A61K 31/713; A61K 9/1635; A61K 9/55561; A61K 2039/57; A61K 2800/51; A61K 31/00; A61K 31/138; A61K 31/155; A61K 31/337; A61K 31/375; A61K 31/421; A61K 31/422; A61K 31/4412; A61K 31/4418; A61K 31/473; A61K 31/485; A61K 31/522; A61K 31/65; A61K 31/7012; A61K 31/704; A61K 31/711; A61K 33/24; A61K 38/05; A61K 38/13; A61K 47/18; A61K 47/20; A61K 47/50; A61K 47/548; A61K 48/0025; A61K 48/0041; A61K 8/4973; A61K 9/0002; A61K 9/10; A61K 9/107; A61K 9/1652; A61K 31/336; A61K 47/60; A61K 47/6907; A61K 9/1075; A61K 47/593; A61K 47/6915; A61K 47/645; A61K 31/7068; A61K 31/7088; A61K 35/39; A61K 49/0013; A61K 9/0012; A61K 9/0021; A61K 2039/545; A61K 31/445; A61K 2039/507; A61K 31/4164; A61K 38/07; A61K 47/6803; A61K 47/6849; A61K 9/0043; A61K 31/166; A61K 31/18; A61K 31/225; A61K 31/351; A61K 31/357; A61K 31/385; A61K 31/403; A61K 31/416; A61K 31/4725; A61K 31/502; A61K 31/573; A61K 31/7036; A61K 31/7048; A61K 31/706; A61K 31/7072; A61K 31/7076; A61K 33/00; A61K 33/242; A61K 33/243; A61K 33/245; A61K 38/08; A61K 38/12; A61K 38/177

See application file for complete search history.

(56) References Cited

FOREIGN PATENT DOCUMENTS

| NO | 2021216749 A1 | 10/2021 |
|---|---|---|
| WO | 2021259673 A1 | 12/2021 |
| WO | 2022053694 A1 | 3/2022 |

OTHER PUBLICATIONS

Achan et al., "Quinine, an old anti-malarial drug in a modern world: role in the treatment of malaria", Malaria Journal 2011, 10:144, 12 pages.

Agnihorti et al., "Formal chemical stability analysis and solubility analysis of artesunate and hydroxychloroquinine for development of parenteral dosage form", Journal of Pharmacy Research 2012, 6(1):117-122.

Alkaloida Chemical Company ZRT. Hydroxychloroquine sulfate tablets. Sep. 15, 2017, 14 pages.

Perrone et al., "Stability data of extemporaneous suspensions of hydroxychloroquine sulphate in oral liquid bases after tablet manipulation", Elsevier, Data in Brief 2020, 33:106575, 6 pages.

Pharmapproach Ltd, "Excipients used in the formulation of lquid dosage forms", Pharmaceutical Technology, Pharmaceutics. Oct. 11, 2020, 7 pages.

Sanofi-Aventis U.S. LLC. Plaquenil® hydroxychloroquine sulfate, USP. Oct. 2006, 8 pages.

Selleckchem. Hydroxychloroquine Sulfate (NSC 4375). Dec. 27, 2022, 2 pages.

Wolk et al. "Provisional in-silico biopharmaceutics classification (BCS) to guide oral drug product development", Drug Design, Development and Therapy 2014, 8, pp. 1563-1575.

D. Lowe, "Chloroquine, Past and Present", Science, Mar. 20, 2020, pp. 1-2.

\* cited by examiner

PHARMACEUTICAL FORMULATIONS OF QUINOLINES

FIELD

The instant disclosure provides liquid pharmaceutical formulations, suitable for oral administration, that comprise cinchona alkaloids or quinolines and that exhibit advantageous stability properties; and provides methods of making and using them.

BACKGROUND

Some report the discovery of quinine as the most serendipitous medical discovery of the 17th century and that the treatment of malaria with quinine marked the first successful use of a chemical compound to treat an infectious disease. Quinine, as a component of the bark of the cinchona (*quina-quina*) tree, was used to treat malaria from as early as the 1600s, when it was referred to as the "Jesuits' bark," "cardinal's bark," or "sacred bark." (See, e.g., Achan et al. Malaria Journal 2011, 10:144.) Quinine is a quinoline, and the chemical structure of quinine is:

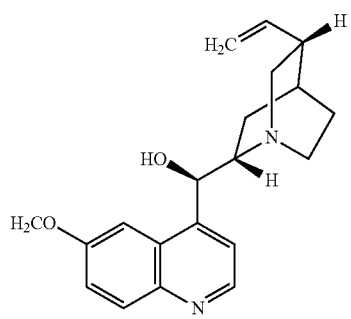

Other cinchona alkaloids that have similar chemical structures to each other and quinine and that also have efficacy in treating malaria include quinidine, cinchonine, dihydroquinine, dihydroquinidine, and cinchonidine. (See, e.g., Achan et al. Malaria Journal 2011, 10:144.)

Some report that quinine was not chemically synthesized until 1944, and there has never been a synthesis that can compete with extraction from its bark. Bayer had started a program to test the company's synthetic compounds for efficacy in treating malaria activity and to make analogs around the active ones. That led in 1934 to the synthesis of chloroquine ("CQ") by Hans Andersag at Bayer. (See, e.g., Lowe, *Chloroquine, Past and Present*. Science: 20 Mar. 2020) The chemical structure of chloroquine is:

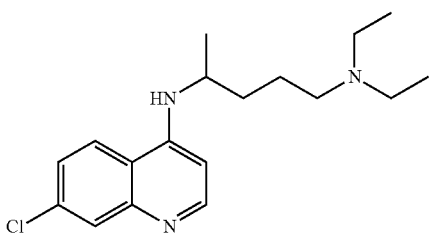 [SMILES: CCN(CC)CCCC(C)Nc1ccnc2cc(Cl)ccc12]

CQ was and continues to be used for the treatment of malaria and is on the World Health Organization's list of essential medicines.

Hydroxychloroquine ("HCQ") was approved for medical use in the United States in 1955 and is currently on the World Health Organization's list of essential medicines. HCQ is the active pharmaceutical ingredient in PLAQUENIL®, which is a tablet that contains 200 mg HCQ and that is indicated for the treatment of uncomplicated malaria due to *Plasmodium falciparum*, rheumatoid arthritis, lupus erythematosus, and chronic discoid lupus erythematosus. PLAQUENIL® is also indicated for the pprophylaxis of malaria in geographic areas where chloroquine resistance is not reported. HCQ is chemically described as 2-[[4-[(7-Chloro-4-quinolyl)amino]pentyl] ethylamino] ethanol sulfate (1:1) with the molecular formula $C_{18}H_{26}ClN_3O \cdot H_2SO$. The chemical structure of HCQ is:

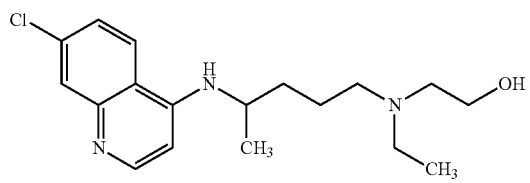 [SMILES: CCN(CCO)CCCC(C)Nc1ccnc2cc(Cl)ccc12]

A side-by-side depiction of CQ, HQC, and quinine is:

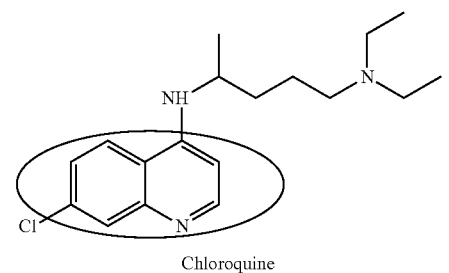

Chloroquine

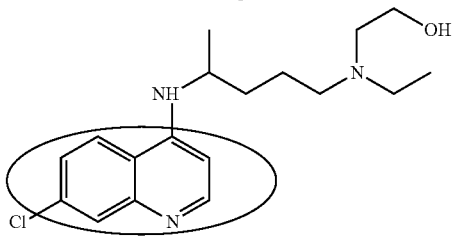

Hydroxychloriquine

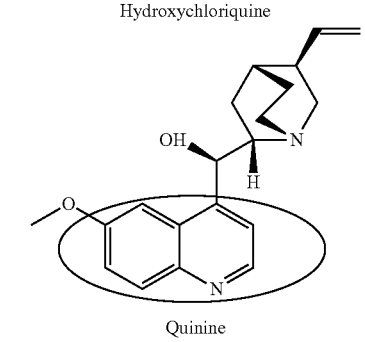

Quinine

Patent Cooperation Treaty Patent Application Publication WO 2021/259673 (the "'673 publication") describes HCQ's mechanism of action as being complex. The '673 publication recites that HCQ decreases pro-inflammatory cytokine secretion, impairs immune cell function, reverses platelet activation induced by human antiphospholipid antibodies, protects the annexin A5 anticoagulant shield from disruption by antiphospholipid antibodies, and markedly suppresses the TLR9-mediated human B cell functions during inflammatory processes.

Perrone et al. discloses that HCQ tablets cannot be administered to non-cooperative patients, such as those in intensive care units or, more in general, unable to swallow solid dosage forms. Perrone et al. further discloses that the hospital pharmacist must manipulate the solid dosage form for the preparation of suspension, even if it can strongly affect the product quality. (Perrone et al. *Stability data of extemporaneous suspensions of hydroxychloroquine sulphate in oral liquid bases after tablet manipulation*. Science Direct, Data in Brief, Volume 33, December 2020, 106575.) Similarly, the '673 publication recites that children under six years old and geriatric populations have difficulties in swallowing tablets. For those populations, the tablets are crushed to a powder that is then dissolved in some beverage such as fruit juice or water and administered to the patient. The '673 publication recites that this practice leads to major problems concerning dosage accuracy and thus the drug efficacy.

SUMMARY

Certain embodiments of the present disclosure provide liquid pharmaceutical formulations, suitable for oral administration, that can include from 10 mg/ml to 100 mg/ml of an active pharmaceutical ingredient (API) that is a cinchona alkaloid, or quinoline such as CQ or HCQ; a solvent that is at least one of glycerin, a propylene glycol (PG), and a polyethylene glycol (PEG); and a carbonate or bicarbonate. In such formulations, each of the solvent and the carbonate are present in the formulations in amounts sufficient to inhibit hydrogen peroxide mediated oxidative degradation of the cinchona alkaloid or quinoline such as CQ or HCQ. In such formulations, the amount of an oxidative degradant N-oxide 1 (e.g., HCQ N-oxide) of a cinchona alkaloid, or quinoline such as CQ or HCQ, produced in the hydrogen peroxide mediated oxidative degradation experiment described in Example 1 is substantially less than produced in a second formulation that differs only by lacking the carbonate or bicarbonate. For instance, such a formulation produces between 2×, 3×, 4×, 5×, 6×, 7×, 8×, 9×, 10×, 11×, 12×, 13×, 14×, or 15×, and 20×, 50×, 100×, or 200× less oxidative degradant N-oxide (e.g., HCQ N-oxide) of the cinchona alkaloid, or quinoline such as CQ or HCQ, than does a second formulation lacking only the carbonate at days 1 or 7 at 60° C. in the hydrogen peroxide mediated oxidative degradation experiment described in below Example 1. Also in such formulations, the amount of assay drop of a cinchona alkaloid, or quinoline such as CQ or HCQ, exhibited in the oxidative degradation experiment described in Example 1 is substantially less than exhibited by a second formulation that differs only by lacking the carbonate or bicarbonate. For instance, such a formulation according to the present disclosure exhibits an assay drop of about 2.5%, 5%, 10%, 15%, 20%, 25%, 30%, or in a range between any two of said assay drop amounts, at day 7 at 60° C. in the oxidative degradation experiment described in Example 1.

In some of such formulations exhibiting less assay drop, the cinchona alkaloid is quinine, quinidine, cinchonine, dihydroquinine, dihydroquinidine, cinchonidine, quinolone, or a combination thereof.

Formulations exhibiting less assay drop can contain from 0.001 mg/ml to 5 mg/ml of the carbonate, which can be one or more of odium carbonate, potassium carbonate, calcium carbonate, magnesium carbonate, ammonium carbonate, sodium bicarbonate, potassium bicarbonate, calcium bicarbonate, magnesium bicarbonate, and ammonium bicarbonate.

Formulations exhibiting less assay drop can also contain from 500 mg/ml to 1,250 mg/ml of a solvent.

Some formulations exhibiting less assay drop can also contain from 0.1% w/v to 2.5% w/v of a divalent chelating agent that is one or more of ethylenediaminetetraacetic acid (EDTA), ethylene glycol tetraacetic acid (EGTA), and ethylenediamine-N,N'-disuccinic acid (EDDS).

Some formulations exhibiting less assay drop can also contain at least one, two, three, or four of, or all of, (i), (ii), (iii), (iv), and (v): (i) from 0.1% w/v to 10% of a sweetener that is at least one of acesulfame-K, advantame, alitame, aspartame, brazzein, carrelame, curculin, a cyclamic acid, a corn syrup, a cyclamate, a dihydrochalchone, erythritol, fructose, galactose, glucose, glycine, a glycyrrhizic acid, a hydrogenated glucose syrup, a hydrogenated starch hydrolysate, isomalt, a lactitol, lactose, mabilin, miraculin, maltitol, maltodextrin, maltose, monatin, mannitol, mannose, mogrosides, monellin, neohesperidin, pentadin, saccharin, sorbitol, stevia, sucralose, sucrose, tagatose, tryptophan, and xylitol; (ii) from 0.1% w/v to 10% of a flavorant that is at least one of a chocolate, a vanilla, a caramel, an orange, a lemon, a lime, a strawberry, a raspberry, a blueberry, a cinnamon, and a nutmeg flavorant; (iii) from 0.1% w/v to 10% of a preservative that is least one of dibutylhydroxytoluene, benzalkonium chloride, benzyl alcohol, a borate, a paraben, cresol, benzoic acid, phenol, sorbic acid, benzethonium chloride, and sodium chlorite; (iv) from 0.1% w/v to 10% of at least one of calcium chloride, magnesium chloride, potassium chloride, sodium chloride, and sodium sulfate Some formulations exhibiting less assay drop can also contain a pH adjusting agent, in an amount of sufficient to yield a pH of the formulation of from 6 to 10, that is one or more of sodium hydroxide, potassium hydroxide, citric acid, and hydrochloric acid. In some such formulations, the API is one or both of hydroxyquinoline or hydroxychloroquine.

Certain embodiments of the present disclosure provide liquid pharmaceutical formulations, suitable for oral administration, that contain of from 10 mg/ml to 100 mg/ml of a cinchona alkaloid, or quinoline such as CQ or HCQ; a solvent that is at least one of glycerin, propylene glycol (PG), and a polyethylene glycol (PEG); and a divalent cation chelating agent that is at least one of an EDTA, an EGTA, and an EDDS. In such formulations, the solvent and the divalent cation chelating agent are present in the formulations in amounts sufficient to inhibit hydrogen peroxide mediated degradation of the cinchona alkaloid, or quinoline such as CQ or HCQ. In such formulations, the amount of an oxidative degradant N-oxide 1 (e.g., HCQ N-oxide) of a cinchona alkaloid, or quinoline such as CQ or HCQ, produced in the hydrogen peroxide mediated oxidative degradation experiment described in Example 1 is substantially less than produced in a second formulation that differs only by lacking the divalent cation chelating agent. For instance, such formulations exhibit between 2×, 3×, 4×, 5×, 6×, 7×, 8×, 9×, 10×, 11×, 12×, 13×, 14×, or 15×, and 20×, 50×, 100×, or 200× less oxidative degradant N-oxide (e.g., HCQ N-oxide) of the cinchona alkaloid, or quinoline such as CQ or HCQ, than does the formulation differing only by lacking the chelating agent at days 1 or 7 at 60° C. in the hydrogen peroxide mediated oxidative degradation experiment described in Example 1. Also in such formulations, the amount of assay drop of a cinchona alkaloid, or quinoline such as CQ or HCQ, exhibited in the oxidative degradation experiment described in Example 1 is substantially less than exhibited by a second formulation that differs only by lacking the divalent cation chelating agent. For instance, such a formulation according to the present disclosure exhibits an assay drop of about 2.5%, 5%, 10%, 15%, 20%, 25%, 30%, or in a range between any two of said assay drop amounts, at day 7 at 60° C. in the oxidative degradation experiment described in Example 1.

In some of such formulations, the cinchona alkaloid is one or more of quinine, quinidine, cinchonine, dihydroquinine, dihydroquinidine, cinchonidine, and quinolone. Some of such formulations contain 40% w/v to 80% w/v of the solvent. Some of such formulations contain from 0.1% w/v to 2.5% w/v of the divalent cation chelating agent.

Some of such formulations contain from 0.001 mg/ml to 5 mg/ml of a carbonate or bicarbonate, which can be one or more of a sodium carbonate, potassium carbonate, calcium carbonate, magnesium carbonate, ammonium carbonate, sodium bicarbonate, potassium bicarbonate, calcium bicarbonate, magnesium bicarbonate, and ammonium bicarbonate.

Some of such formulations contain at least one, two, three, or four of, or all of, (i), (ii), (iii), (iv), and (v): (i) from 0.1% w/v to 10% of a sweetener that is at least one of acesulfame-K, advantame, alitame, aspartame, brazzein, carrelame, a curculin, a cyclamic acid, a corn syrup, cyclamate, dihydrochalchone, erythritol, fructose, galactose, glucose, glycine, glycyrrhizic acid, a hydrogenated glucose syrup, a hydrogenated starch hydrolysate, isomalt, lactitol, lactose, mabilin, miraculin, maltitol, maltodextrin, maltose, monatin, mannitol, mannose, mogrosides, monellin, neohesperidin, pentadin, saccharin, sorbitol, stevia, sucralose, sucrose, tagatose, tryptophan, and xylitol; (ii) from 0.1% w/v to 10% of a flavorant that is at least one of a chocolate, a vanilla, a caramel, an orange, a lemon, a lime, a strawberry, a raspberry, a blueberry, a cinnamon, and a nutmeg flavorant; (iii) from 0.1% w/v to 10% of a preservative that is least one of dibutylhydroxytoluene, benzalkonium chloride, benzyl alcohol, borate, a paraben, cresol, benzoic acid, phenol, sorbic acid, benzethonium chloride, and sodium chlorite; (iv) from 0.1% w/v to 10% of at least one of calcium chloride, magnesium chloride, potassium chloride, sodium chloride, and sodium sulfate; and (v) a pH adjusting agent, in an amount of sufficient to yield a pH of the formulation of from 6 to 10, that is one or more of sodium hydroxide, potassium hydroxide, citric acid, and hydrochloric acid. In some such formulations, the API is one or both of the hydroxyquinoline or the hydroxychloroquine.

Certain embodiments of the present disclosure provide liquid pharmaceutical formulations, suitable for oral administration, that can include from 10 mg/ml to 100 mg/ml of a cinchona alkaloid, quinoline, CQ or HCQ, one or more pharmaceutically acceptable salts thereof, or a combination thereof a solvent that is at least one of glycerin and propylene glycol (PG); a carbonate; and a divalent cation chelating agent that is at least one of EDTA, EGTA, and EDDS. In such formulations, each of the solvent, the carbonate, and the divalent cation chelating agent are present in the formulation in amounts sufficient to inhibit hydrogen peroxide mediated oxidative degradation of the cinchona alkaloid, quinoline, CQ or HCQ. In such formulations, the amount of an oxidative degradant N-oxide 1 (e.g., HCQ N-oxide) of a cinchona alkaloid, quinoline, CQ or HCQ produced in the oxidative degradation experiment described in Example 1 is substantially less than produced in a second formulation that differs only by lacking the carbonate and the divalent cation chelating agent. For instance, such the formulation of the present disclosure produces from 2×, 3×, 4×, 5×, 6×, 7×, 8×, 9×, 10×, 11×, 12×, 13×, 14×, or 15× to 20×, 50×, 100×, or 200× less oxidative degradant N-oxide (e.g., HCQ N-oxide) of the cinchona alkaloid, quinoline, CQ or HCQ than does a second formulation that differs only by lacking the carbonate and the divalent cation chelating agent at days 1 or 7 at 60° C. in the oxidative degradation experiment described in Example 1. Also in such formulations, the amount of assay drop of a cinchona alkaloid, quinoline, CQ or HCQ exhibited in the oxidative degradation experiment described in Example 1 is substantially less than exhibited by a second formulation that differs only by lacking the carbonate and the divalent cation chelating agent. For instance, such a formulation according to the present disclosure exhibits an assay drop of about 2.5%, 5%, 10%, 15%, 20%, 25%, 30%, or in a range between any two of said assay drop amounts, at day 7 at 60° C. in the oxidative degradation experiment described in Example 1.

In some of such formulations, the cinchona alkaloid is at least one of quinine, quinidine, cinchonine, dihydroquinine, dihydroquinidine, cinchonidine, quinolone, one or more pharmaceutical salt(s) thereof, or a combination thereof and wherein the quinoline is chloroquine, hydroxychloroquine, one or more pharmaceutical salt(s) thereof, or a combination thereof.

Some of such formulations contain from 0.1% w/v to 2.5% w/v of the divalent cation chelating agent. Some of such formulations contain from 40% w/v to 80% w/v of the solvent. Some of such formulations contain from 0.001 mg/ml to 5 mg/ml of the carbonate, which can be one or more of a sodium carbonate, potassium carbonate, calcium carbonate, magnesium carbonate, ammonium carbonate, sodium bicarbonate, potassium bicarbonate, calcium bicarbonate, magnesium bicarbonate, and ammonium bicarbonate.

Some of such formulations contain at least one, two, three, or four of, or all of, (i), (ii), (iii), (iv), and (iv): (i) from 0.1% w/v to 10% of a sweetener that is at least one acesulfame-K, advantame, alitame, aspartame, brazzein, carrelame, curculin, cyclamic acid, a corn syrup, cyclamate, dihydrochalchone, erythritol, fructose, galactose, glucose, glycine, glycyrrhizic acid, hydrogenated glucose syrup, hydrogenated starch hydrolysate, isomalt, lactitol, lactose, mabilin, miraculin, maltitol, maltodextrin, maltose, monatin, mannitol, mannose, mogrosides, monellin, neohesperidin, pentain, saccharin, sorbitol, stevia, sucralose, sucrose, tagatose, tryptophan, and xylitol; (ii) from 0.1% w/v to 10% of a flavorant that is at least one of chocolate, vanilla, caramel, orange, lemon, lime, strawberry, raspberry, blueberry, cinnamon, and nutmeg; (iii) from 0.1% w/v to 10% of a preservative that is least one of a dibutylhydroxytoluene, benzalkonium chloride, benzyl alcohol, borate, paraben, cresol, benzoic acid, phenol, sorbic acid, benzethonium chloride, and sodium chlorite; (iv) from 0.1% w/v to 10% of at least one of calcium chloride, magnesium chloride, potassium chloride, sodium chloride, and sodium sulfate; and (v) a pH adjusting, in an amount of sufficient to yield a pH of the formulation of from 6 to 10, that is one or more of sodium hydroxide, potassium hydroxide, citric acid, and hydrochloric acid. In some such formulations, the quinoline is one or both of hydroxyquinoline and hydroxychloroquine.

Certain embodiments of the disclosure provide liquid pharmaceutical formulations, suitable for oral administration, that can include: from 30 mg/ml to 50 mg/ml of one or both of chloroquine and hydroxychloroquine; from 1000 mg/ml to 1250 mg/ml of a solvent that one or more of glycerin, PG, and a PEG; from 0.1 mg/ml to 1 mg/ml a carbonate that is one or more of sodium carbonate, potassium carbonate, calcium carbonate, magnesium carbonate, ammonium carbonate, sodium bicarbonate, potassium bicarbonate, calcium bicarbonate, magnesium bicarbonate, and ammonium bicarbonate; and at least two, three, or four of, or all of, (i), (ii), (iii), (iv), and (iv): from 0.1% w/v to 10% of a sweetener that is at least one of acesulfame-K, advantame, alitame, aspartame, brazzein, carrelame, curculin, cyclamic acid, a corn syrup, cyclamate, dihydrochalchone, erythritol, fructose, galactose, glucose, glycine, glycyrrhizic acid, a hydrogenated glucose syrup, a hydrogenated starch hydrolysate, isomalt, lactitol, lactose, mabilin, miraculin, maltitol, maltodextrin, maltose, monatin, mannitol, mannose, mogrosides, monellin, neohesperidin, pentadin, saccharin, sorbitol, stevia, sucralose, sucrose, tagatose, tryptophan, and xylitol; (ii) from 0.1% w/v to 10% of a flavorant that is at least one of a chocolate, a vanilla, a caramel, an orange, a lemon, a lime, a strawberry, a raspberry, a blueberry, a cinnamon, and a nutmeg flavorant; (iii) from 0.1% w/v to 10% of a preservative that is least one of dibutylhydroxytoluene, benzalkonium chloride, benzyl alcohol, a borate, a paraben, cresol, benzoic acid, phenol, sorbic acid, benzethonium chloride, and sodium chlorite; (iv) from 0.1% w/v to 10% of at least one of calcium chloride, magnesium chloride, potassium chloride, sodium chloride, and sodium sulfate; and (v) a pH adjusting, in an amount of sufficient to yield a pH of the formulation of from 6 to 10, that is one or more of sodium hydroxide, potassium hydroxide, citric acid, and hydrochloric acid. Some of such formulations contain from 1% w/v to 5% of lemon and lime flavorant. In some of such formulations, the pH adjusting agent is citric acid. In some of such formulations, the solvent is glycerin. In some of such formulations, the carbonate is sodium carbonate. Some of such formulations contain from 0.1% w/v to 2.5% w/v of one or more of EDTA, EGTA, and EDDS.

Certain embodiments of the disclosure provide liquid pharmaceutical formulations, suitable for oral administration, that can include about 40 mg/ml of a hydroxychloroquine sulfate; about 0.035% w/v of sodium carbonate; about 60% w/v of glycerin; about 1% w/v of EDTA; about 4% w/v of sucralose. about 2% w/v of a flavorant that is a mixture of lemon and lime flavors; and an amount of citric acid sufficient to adjust the pH of the formulation to from about pH 6 to about pH 10.

Certain embodiments of the disclosure provide methods of treating uncomplicated malaria due to *Plasmodium falciparum*, rheumatoid arthritis, lupus erythematosus, or chronic discoid lupus erythematosus, that can include a step of orally administering a formulation of the disclosure to a subject presenting uncomplicated malaria due to *Plasmodium falciparum*, rheumatoid arthritis, lupus erythematosus, and chronic discoid lupus erythematosus.

DETAILED DESCRIPTION

The present disclosure provides liquid pharmaceutical formulations of a cinchona alkaloid, a quinoline, CQ or HCQ that are suitable for oral administration and that exhibit surprisingly advantageous properties such as resistance to oxidative degradation of the cinchona alkaloid mediated by free radicals and/or free radical generating agents, including without limitation hydrogen peroxide. Without limitation, unexpectedly beneficial properties demonstrated by formulations of the instant disclosure include not only significantly reduced impurity generation regarding the cinchona alkaloid, quinoline, CQ or HCQ in the formulations but also significantly reduced assay drop (that is, a reduction in the amount of the intact API assayable in the formulation.)

Exemplary cinchona alkaloids useful in liquid formulations of the present disclosure include, without limitation, quinine, quinidine, cinchonine, dihydroquinine, dihydroquinidine, cinchonidine, quinolone, and hydroxyquinoline.

Such formulations of the disclosure comprising one or more cinchona alkaloids and/or quinolines are useful for treating uncomplicated malaria due to *Plasmodium falciparum*, rheumatoid arthritis, lupus erythematosus, and chronic discoid lupus erythematosus and for the prophylaxis of malaria in geographic areas where chloroquine resistance is not reported.

Formulations as disclosed herein can "comprise" a list of ingredients, such list then being open to inclusion of further unspecified ingredients. Alternatively, formulations as disclosed herein can "consist of" a list of ingredients, meaning that the formulations include only the listed ingredients. Formulations as disclosed herein can also "consist essentially of" the listed ingredients, meaning that the formulations include all of the listed ingredients, and may include as well any further ingredients that do not affect the utility of the formulation. In the instance of the present disclosure, that utility is reducing oxidative degradation of the API and reducing oxidative impurity generation.

In some embodiments, formulations of the disclosure can include one or more of a cinchona alkaloid or quinoline, such as quinine, quinidine, cinchonine, dihydroquinine, dihydroquinidine, cinchonidine, quinolone, chloroquine, hydroxychloroquine, or a pharmaceutically acceptable salt thereof, in amounts of from 0.5 mg/ml to 100 mg/ml. Exemplary particular concentrations of cinchona alkaloid, such as quinine, quinidine, cinchonine, dihydroquinine, dihydroquinidine, cinchonidine, quinolone, chloroquine, and hydroxychloroquine, or a pharmaceutically acceptable salt thereof that are useful in formulations of the disclosure include 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 12.5 mg/ml, 15 mg/ml, 17.5 mg/ml, 20 mg/ml, 22.5 mg/ml, 25 mg/ml, 27.5 mg/ml, 30 mg/ml, 32.5 mg/ml, 35 mg/ml, 37.5 mg/ml, 40 mg/ml, 42.5 mg/ml, 45 mg/ml, 47.5 mg/ml, 50 mg/ml, 52.5 mg/ml, 55 mg/ml, 57.5 mg/ml, 60 mg/ml, 62.5 mg/ml, 65 mg/ml, 67.5 mg/ml, 70 mg/ml, 72.5 mg/ml, 75 mg/ml, 77.5 mg/ml, 80 mg/ml, 82.5 mg/ml, 85 mg/ml, 87.5 mg/ml, 90 mg/ml, 92.5 mg/ml, 95 mg/ml, 97.5 mg/ml, or 100 mg/ml, as well as in a range between any two of said cinchona alkaloid concentrations.

In some embodiments, formulations of the disclosure can include a cinchona alkaloid and/or a quinoline, such as quinine, quinidine, cinchonine, dihydroquinine, dihydroquinidine, cinchonidine, quinolone, chloroquine, and hydroxychloroquine, or a pharmaceutically acceptable salt thereof, in weight to volume proportions of from 0.5% w/v to 20% w/v and exemplary particular weight to volume proportions include 0.5% w/v, 1% w/v, 1.25% w/v, 1.5% w/v, 1.75% w/v, 2% w/v, 2.25% w/v, 2.5% w/v, 2.75% w/v, 3% w/v, 3.25% w/v, 3.5% w/v, 3.75% w/v, 4% w/v, 4.25% w/v, 4.5% w/v, 4.75% w/v, 5% w/v, 5.25% w/v, 5.5% w/v, 5.75% w/v, 6% w/v, 7.25% w/v, 7.5% w/v, 7.75% w/v, 8% w/v, 8.25% w/v, 8.5% w/v, 8.75% w/v, 9% w/v, 10% w/v, 11% w/v, 12% w/v, 13% w/v, 14% w/v, 15% w/v, 16% w/v, 17% w/v, 18% w/v, 19% w/v, or 20% w/v, as well as in a range between any two of said weight to volume proportions.

In some embodiments, cinchona alkaloid and/or quinoline added to a formulation of the present disclosure has an initial purity of at least 90% w/w, for example at least: 90% w/w, 91% w/w, 92% w/w, 93% w/w, 94% w/w, 95% w/w, 96% w/w, 97% w/w, 98% w/w, or 99% w/w.

In some embodiments, formulations of the disclosure can include a proportion of the cinchona alkaloid, or a pharmaceutically acceptable salt thereof, that is dissolved in a liquid solvent (i.e., in solution) that is at least: 10%, 20%, 30%, 40%, 50%, 60%, 70%, 75%, 80%, 85%, 90%, 91%, 92%, 93%, 94%, 95%, 96%, 97%, 98%, or 99%.

In some embodiments, formulations of the disclosure can include a solvent. Solvents useful in the formulation include glycerin, propylene glycol, polyethylene glycol, and combinations thereof. Such solvents may be included in formulations of the disclosure in weight to volume proportions of 20% w/v, 25% w/v, 30% w/v, 35% w/v, 40% w/v, 45% w/v, 50% w/v, 55% w/v, 60% w/v, 65% w/v, 70% w/v 75% w/v, 80% w/v, 85% w/v, 90% w/v, 95% w/v, 100% w/v, 105% w/v, 110% w/v, 115% w/v, 120% w/v, 125% w/v, 130% w/v, 135% w/v, 140% w/v, or in a range between any two of said solvent proportions. The formulations may comprise combinations of solvents, in amounts that individually or in aggregate achieve(s) the stated weight to volume proportions. Such solvents may be included in formulations of the disclosure in concentrations of 50 mg/ml, 60 mg/ml, 70 mg/ml, 80 mg/ml, 90 mg/ml, 100 mg/ml, 150 mg/ml, 200 mg/ml, 250 mg/ml, 300 mg/ml, 350 mg/ml, 400 mg/ml, 500 mg/ml, 550 mg/ml, 600 mg/ml, 650 mg/ml, 700 mg/ml, 750 mg/ml, 800 mg/ml, 850 mg/ml, 900 mg/ml, 950 mg/ml, 1000 mg/ml, 1050 mg/ml, 1100 mg/ml, 1150 mg/ml, 1200 mg/ml, and 1260 mg/ml, as well as in a range between any two of said solvent concentrations.

In some embodiments, formulations of the disclosure can include a carbonate. Carbonates useful in the formulations of the present disclosure include sodium carbonate, potassium carbonate, calcium carbonate, magnesium carbonate, ammonium carbonate, sodium bicarbonate, potassium bicarbonate, calcium bicarbonate, magnesium bicarbonate, ammonium bicarbonate, or a combination thereof. The carbonate may be present in liquid pharmaceutical formulations of the disclosure in amount effective to inhibit degradation of the cinchona alkaloid, quinolone, CQ or HCQ mediated by free radicals and/or free radical generating agents, such as without limitation hydrogen peroxide. In such embodiments, formulations of the disclosure may comprise carbonates in concentrations of from 0.001 mg/ml to 5 mg/ml, and particular concentrations of carbonates useful in formulations of the disclosure include 0.001 mg/ml, 0.0025 mg/ml, 0.005 mg/ml, 0.0075 mg/ml, 0.01 mg/ml, 0.025 mg/ml, 0.05 mg/ml, 0.075 mg/ml, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, 1.5 mg/ml, 2 mg/ml, 2.5 mg/ml, 3 mg/ml, 3.5 mg/ml, 4 mg/ml, 4.5 mg/ml, and 5 mg/ml, as well as in a range between any two of said carbonate concentrations. The formulations may comprise combinations of any two or more carbonates, in amounts that individually or in aggregate achieve(s) the stated carbonate concentrations.

In some embodiments, formulations of the disclosure can include one or more divalent ion chelating agents such as, without limitation, ethylenediaminetetraacetic acid ("EDTA"), ethylene glycol tetraacetic acid ("EGTA"), ethylenediamine-N,N'-disuccinic acid ("EDDS"), or a combination thereof. The divalent chelating agent may be present in a liquid pharmaceutical formulation of the disclosure in an amount effective to inhibit degradation of the cinchona alkaloid mediated by free radicals and/or free radical generating agents, such as, without limitation hydrogen peroxide. In such embodiments, the divalent cation chelating agent (e.g., EDTA, EGTA, and EDDS) or combination thereof is present in liquid formulations of the disclosure in weight to volume proportions of from 0.5% w/v to 10% w/v, and particular proportions include 0.01% w/v, 0.05% w/v, 0.075% w/v, 0.1% w/v, 0.5% w/v, 0.75% w/v, 1% w/v, 1.5% w/v, 2% w/v, 2.5% w/v, 3% w/v, 3.5% w/v, 4% w/v, 4.5% w/v, 5% w/v, 5.5% w/v, 6% w/v, 7.5% w/v, 8% w/v, 8.5% w/v, 9% w/v, 9.5% w/v, 10% w/v, as well as in a range between any two of said divalent chelating agent proportions. The formulations may comprise combinations of divalent chelating agents in amounts that individually or in aggregate achieve(s) the stated weight to volume proportions.

In some embodiments, formulations of the disclosure can include a sweetener. Sweeteners useful in the formulations of the present disclosure include acesulfame-K, advantame, alitame, aspartame, brazzein, carrelame, curculin, cyclamic acid, corn syrup (e.g., high fructose corn syrup), cyclamate, dihydrochalchone, erythritol, fructose, galactose, glucose, glycerin, glycine, glycyrrhizic acid, hydrogenated glucose syrup, hydrogenated starch hydrolysate, isomalt, lactitol, lactose, mabilin, miraculin, maltitol, maltodextrin, maltose, monatin, mannitol, mannose, mogrosides, monellin, neohesperidin, pentadin, saccharin, sorbitol, *stevia* glycosides, sucralose, sucrose, tagatose, tryptophan, and xylitol. The sweetener may be present in liquid pharmaceutical formulations of the disclosure in weight to volume proportions of 0.10% w/v, 0.15% w/v, 0.20% w/v, 0.25% w/v, 0.30% w/v, 0.35% w/v, 0.40% w/v, 0.45% w/v, 0.50% w/v, 0.55% w/v, 0.60% w/v, 0.65% w/v, 0.70% w/v 0.75% w/v, 0.80% w/v, 80.5% w/v, 0.90% w/v, 0.95% w/v, 1% w/v, 2% w/v, 3% w/v, 4% w/v, 5% w/v, 6% w/v, 7% w/v, 8% w/v, 9% w/v, 10% w/v or in a range between any two of said sweetener proportions. The formulations may comprise combinations of sweeteners, in amounts that individually or in aggregate achieve(s) the stated weight to volume proportions.

In some embodiments, formulations of the disclosure can include a flavorant. Flavorants useful in the formulations of the present disclosure include chocolate, vanilla, caramel, orange, lemon, lime, strawberry, raspberry, blueberry, cinnamon, and nutmeg flavorants. The flavorant may be present in liquid pharmaceutical formulations of the disclosure in weight to volume proportions of 0.10% w/v, 0.15% w/v, 0.20% w/v, 0.25% w/v, 0.30% w/v, 0.35% w/v, 0.40% w/v, 0.45% w/v, 0.50% w/v, 0.55% w/v, 0.60% w/v, 0.65% w/v, 0.70% w/v 0.75% w/v, 0.80% w/v, 80.5% w/v, 0.90% w/v, 0.95% w/v, 1% w/v, 2% w/v, 3% w/v, 4% w/v, 5% w/v, 6% w/v, 7% w/v, 8% w/v, 9% w/v, 10% w/v or in a range between any two of said flavorant proportions. The formulations may comprise combinations of flavorant, in amounts that individually or in aggregate achieve(s) the stated weight to volume proportions.

In some embodiments, formulations of the disclosure can include a pH adjusting agent. pH adjusting agents useful in the formulations of the present disclosure include sodium hydroxide, potassium hydroxide, citric acid, and hydrochloric acid. Compositions of the present disclosure may contain amounts of pH adjusting agents sufficient to achieve a pH of 6 to 10, for example pH 6, pH 6.1, pH 6.2, pH 6.3, pH 6.4, pH 6.5, pH 6.6, pH 6.7, pH 6.8, pH 6.9, pH 7, pH 7.1, pH 7.2, pH 7.3, pH 7.4, pH 7.5, pH 7.6, pH 7.7, pH 7.8, pH 7.9, pH 8, pH 8.1, pH 8.2, pH 8.3, pH 8.4, pH 8.5, pH 8.6, pH 8.7, pH 8.8, pH 8.9, pH 9, pH 9.1, pH 9.2, pH 9.3, pH 9.4, pH 9.5, pH 9.6, pH 9.7, pH 9.8, pH 9.9, pH 10, pH 9, pH 9.1, pH 9.2, pH 9.3, pH 9.4, pH 9.5, pH 9.6, pH 9.7, pH 9.8, pH 9.9, pH 10, pH 10.1, pH 10.2, pH 10.3, pH 10.4, pH 10.5, pH 10.6, pH 10.7, pH 10.8, pH 10.9, pH 11 or in a range between any two such pH values.

In some embodiments, formulations of the present disclosure are pourable. The viscosities of such formulations can range from 1 centipoise ("cps") (i.e., the viscosity of water at room temperature) to 25,000 cps (i.e., the viscosity of chocolate syrup at room temperature); and exemplary particular viscosities of formulations of the disclosure include 1 cps, 25 cps, 50 cps, 75 cps, 100 cps, 150 cps, 200 cps (about the viscosity of maple syrup at room temperature), 250 cps, 300 cps, 400 cps, 500 cps, 600 cps, 700 cps, 800 cps, 900 cps, 1000 cps (about the viscosity of glycerin at room temperature), 1100 cps, 1200 cps, 1300 cps, 1400 cps, 1500 cps, 1600 cps, 1700 cps, 1800 cps, 1900 cps, 2000 cps, 2100 cps, 2200 cps, 2300 cps, 2400 cps, 2500 cps, 2600 cps, 2700 cps, 2800 cps, 2900 cps, 3000 cps, 3500 cps, 4000 cps, 4500 cps, 5000 cps, 6000 cps, 7000 cps, 8000 cps, 9000 cps, 10,000 cps, 12,500 cps, 15,000 cps, 17,500 cps, 20,000, cps 22,500 cps, 25,000 cps (about the viscosity of chocolate syrup at room temperature), 27,500 cps, 30,000, cps as well as in a range between any two of said viscosities.

In some embodiments, formulations of the disclosure can include a polymer. Non-ionic polymers useful in certain formulations of the disclosure include hydroxyethyl cellulose, hydroxypropylmethyl cellulose, methyl cellulose, carboxymethyl cellulose, polyvinyl pyrrolidone, and polyvinyl alcohol. Ionic polymers useful in certain formulations of the disclosure include polyacrylates (e.g., carbopols and carbomers), alginates, chitosans, hyaluronic acid, and xanthan gum. Such ionic and/or nonionic polymers may be included in formulations of the disclosure in weight to volume proportions of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, 5.0% w/v, or in a range between any two of said polymer proportions. The formulations may comprise combinations of polymers, in amounts that individually or in aggregate achieve(s) the stated weight to volume proportions.

In some embodiments, formulations of the disclosure can include a surfactant. Surfactants useful in certain formulations of the disclosure include sodium lauryl sulfate, docusate sodium, phosphatidylcholine, lecithin, betaines, tyloxapol, polyoxyethylene sorbitan esters, such as polysorbate 20, polysorbate 60, and polysorbate 80; polyethoxylated castor oils, such as cremaphor, polyethoxylated hydrogenated castor oils, such as HCO-40; and poloxamers. The formulations may comprise surfactant in weight to volume proportions of 0.001% w/v, 0.005% w/v, 0.01% w/v, 0.05% w/v, 0.1% w/v, 0.2% w/v, 0.3% w/v, 0.4% w/v, 0.5% w/v, 0.6% w/v, 0.7% w/v, 0.8% w/v, 0.9% w/v, 1.0% w/v, 1.1% w/v, 1.2% w/v, 1.3% w/v, 1.4% w/v, 1.5% w/v, 1.6% w/v, 1.7% w/v, 1.8% w/v, 1.9% w/v, 2.0% w/v, or in a ranges between any two of said surfactant proportions. The formulations may comprise combinations of surfactants, in amounts that individually or in aggregate achieve(s) the stated weight to volume proportions.

In some embodiments, formulations of the disclosure can include a tonicity agent. Ionic tonicity agents useful in certain formulations of the disclosure include calcium chloride, magnesium chloride, potassium chloride, sodium chloride, sodium sulfate, and combinations thereof. Nonionic tonicity agents useful in the formulations described herein include mannitol, sorbitol, xylitol, erythritol, lactitol, maltitol, isomalt, and combinations thereof. The formulations may comprise tonicity agent in weight to volume proportions of 0.001% w/v, 0.005% w/v, 0.01% w/v, 0.05% w/v, 0.1% w/v, 0.2% w/v, 0.3% w/v, 0.4% w/v, 0.5% w/v, 0.6% w/v, 0.7% w/v, 0.8% w/v, 0.9% w/v, 1.0% w/v, 1.1% w/v, 1.2% w/v, 1.3% w/v, 1.4% w/v, 1.5% w/v, 1.6% w/v, 1.7% w/v, 1.8% w/v, 1.9% w/v, 2.0% w/v, or in a range between any two of said tonicity agent proportions. The formulations may comprise combinations of tonicity agent, in amounts that individually or in aggregate achieve(s) the stated tonicity weight to volume proportions.

In some embodiments, formulations of the disclosure can include a preservative.

Preservatives useful in certain formulations of the disclosure include dibutylhydroxytoluene, benzalkonium chloride, benzyl alcohol, borates, parabens, cresols, benzoic acid, phenol, sorbic acid, benzethonium chloride, sodium chlorite and combinations thereof. The formulations may comprise preservative in weight to volume proportions of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, and 5.0% w/v, or in a range between any two of said preservative proportions. The formulations may comprise combinations of preservatives, in amounts that individually or in aggregate achieve(s) the stated weight to volume proportions.

In some embodiments, a formulation of the disclosure can consist of the cinchona alkaloid or the quinoline, such as CQ and/or HCQ, as the API as described above, glycerine, propylene glycol or a polyethylene glycol as the solvent as described above and a complexing agent as described above. In some embodiments, a formulation of the disclosure can consist of the cinchona alkaloid or a quinoline, such as, CQ and/or HCQ, as the API as described above, glycerine or polyethylene glycol as the solvent as described above, and a carbonate as described above. In some embodiments, a formulation of the disclosure can consist of the cinchona alkaloid or the quinoline, such as, CQ and/or HCQ as the API, glycerine, propylene glycol or polyethylene glycol as the solvent as described above, a carbonate as described above and a complexing agent as described above. In some embodiments, a formulation of the disclosure can consist of the cinchona alkaloid or the quinoline, such as CQ and/or HCQ, as the API as described above, glycerine or propylene glycol or polyethylene glycol as the solvent as described above, and a carbonate as described above, a complexing agent as described above and a pH adjusting agent as described above. In any such embodiments, the pH of the formulation can be from 6 to 11 as described above. In some embodiments, a formulation of the disclosure can consist of the cinchona alkaloid or the quinoline, such as CQ and/or HCQ as the API, glycerine or polyethylene glycol as the solvent, and a carbonate as described above, a complexing agent as described above and a pH adjusting agent as described above and one or more of a sweetener, flavorant, polymer, surfactant, tonicity agent and preservative as described above.

Some Exemplary Embodiments

Some specific, non-limiting embodiments within the present disclosure are enumerated below. This listing of particular embodiments is not intended to limit the scope of the disclosure.

Embodiment 1: A liquid pharmaceutical formulation, suitable for oral administration, comprising:
from 10 mg/ml to 100 mg/ml of an active pharmaceutical ingredient (API) that is a cinchona alkaloid or a quinoline, or one or more pharmaceutically acceptable sat(s) thereof, or a combination thereof;
a solvent that is at least one of a glycerin, propylene glycol (PG), and a polyethylene glycol (PEG); and
a carbonate or a bicarbonate;
wherein each of the solvent and the carbonate are present in the formulation in amounts sufficient to inhibit hydrogen peroxide mediated degradation of the cinchona alkaloid or quinoline.

Embodiment 2: The formulation of Embodiment 1, wherein the formulation comprises 0.001 mg/ml to 5 mg/ml of the carbonate and wherein the carbonate is at least one of sodium carbonate, potassium carbonate, calcium carbonate, magnesium carbonate, ammonium carbonate, sodium bicarbonate, potassium bicarbonate, calcium bicarbonate, magnesium bicarbonate, and ammonium bicarbonate.

Embodiment 3: The formulation of Embodiment 1 or Embodiment 2, wherein the formulation comprises 500 mg/ml to 1,250 mg/ml of the solvent.

Embodiment 4: The formulation of any one of Embodiments 1 to 3, wherein the cinchona alkaloid is at least one of quinine, quinidine, cinchonine, dihydroquinine, dihydroquinidine, cinchonidine, quinolone, or one or more pharmaceutically acceptable sat(s) thereof, or a combination thereof and wherein the quinoline is chloroquine, hydroxychloroquine, or one or more pharmaceutically acceptable sat(s) thereof, or a combination thereof.

Embodiment 5: The formulation of any one of Embodiments 1 to 4, further comprising from 0.1% w/v to 2.5% w/v of at least one of ethylenediaminetetraacetic acid (EDTA), ethylene glycol tetraacetic acid (EGTA), and ethylenediamine-N,N'-disuccinic acid (EDDS).

Embodiment 6: The formulation of any one of Embodiments 1 to 5, further comprising at least one of:
(i) from 0.1% w/v to 10% of a sweetener that is at least one of acesulfame-K, advantame, alitame, aspartame, brazzein, carrelame, curculin, a corn syrup, cyclamate, dihydrochalchone, erythritol, fructose, galactose, glucose, glycine, glycyrrhizic acid, a hydrogenated glucose syrup, a hydrogenated starch hydrolysate, isomalt, lactitol, lactose, mabilin, miraculin, maltitol, maltodextrin, maltose, monatin, mannitol, mannose, mogrosides, monellin, neohesperidin, pentadin, saccharin, sorbitol, stevia, sucralose, sucrose, tagatose, tryptophan, and xylitol;
(ii) from 0.1% w/v to 10% of a flavorant is at least one of a chocolate, a vanilla, a caramel, an orange, a lemon, a lime, a strawberry, a raspberry, a blueberry, a cinnamon, and a nutmeg flavorant;
(iii) from 0.1% w/v to 10% of a preservative that is least one of dibutylhydroxytoluene, benzalkonium chloride, benzyl alcohol, a borate, a paraben, cresol, benzoic acid, phenol, sorbic acid, benzethonium chloride, and sodium chlorite;
(iv) from 0.1% w/v to 10% of at least one of calcium chloride, magnesium chloride, potassium chloride, sodium chloride, and sodium sulfate; and
(v) an amount of a pH adjusting sufficient to yield a pH of the formulation of from 6 to 10, wherein the pH adjusting agent is at least one of sodium hydroxide, potassium hydroxide, citric acid, and hydrochloric acid.

Embodiment 7: The formulation of Embodiment 6, wherein the formulation comprises at least two of: (i), (ii), (iii), (iv), and (v).

Embodiment 8: The formulation of Embodiment 6, wherein the formulation comprises at least three of: (i), (ii), (iii), (iv), and (v).

Embodiment 9: The formulation of Embodiment 6, wherein the formulation comprises at least four of: (i), (ii), (iii), (iv), and (v).

Embodiment 10: The formulation of Embodiment 6, wherein the formulation comprises each of: (i), (ii), (iii), (iv), and (v).

Embodiment 11: The formulation of any one of Embodiments 1 to 10, wherein the API is one or both of hydroxyquinoline and hydroxychloroquine.

Embodiment 12: The formulation of any one of Embodiments 1 to 10, wherein the API is hydroxychloroquine.

Embodiment 13: A method of treating uncomplicated malaria due to *Plasmodium falciparum*, rheumatoid arthritis, lupus erythematosus, or chronic discoid lupus erythematosus, comprising orally administering the formulation of any one of Embodiments 1 to 12 to a subject presenting treating uncomplicated malaria due to *Plasmodium falciparum*, rheumatoid arthritis, lupus erythematosus, and chronic discoid lupus erythematosus.

Embodiment 14: A liquid pharmaceutical formulation, suitable for oral administration, comprising:
from 30 mg/ml to 50 mg/ml of at least one of chloroquine and hydroxychloroquine;
from 1,000 mg/ml to 1,250 mg/ml of a solvent that is at least one of glycerin, PG, and a PEG;
from 0.1 mg/ml to 1 mg/ml a carbonate that is at least one of sodium carbonate, potassium carbonate, calcium carbonate, magnesium carbonate, ammonium carbonate, sodium bicarbonate, potassium bicarbonate, calcium bicarbonate, magnesium bicarbonate, and ammonium bicarbonate;
at least two of:
(i) from 0.1% w/v to 10% of a sweetener that is at least one of acesulfame-K, advantame, alitame, aspartame, brazzein, carrelame, curculin, cyclamic acid, a corn syrup, cyclamate, dihydrochalchone, erythritol, fructose, galactose, glucose, glycine, glycyrrhizic acid, a hydrogenated glucose syrup, a hydrogenated starch hydrolysate, isomalt, lactitol, lactose, mabilin, miraculin, maltitol, maltodextrin, maltose, monatin, mannitol, mannose, mogrosides, monellin, neohesperidin, pentadin, saccharin, sorbitol, stevia, sucralose, sucrose, tagatose, tryptophan, and xylitol;
(ii) from 0.1% w/v to 10% of a flavorant that is at least one of a chocolate, a vanilla, a caramel, an orange, a lemon, a lime, a strawberry, a raspberry, a blueberry, a cinnamon, and a nutmeg flavorant;
(iii) from 0.1% w/v to 10% of a preservative that is least one of dibutylhydroxytoluene, benzalkonium chloride, benzyl alcohol, a borate, a paraben, cresols, benzoic acid, phenol, sorbic acid, benzethonium chloride, and sodium chlorite;
(iv) from 0.1% w/v to 10% of at least one of calcium chloride, magnesium chloride, potassium chloride, sodium chloride, and sodium sulfate; and
(v) an amount of a pH adjusting sufficient to yield a pH of the formulation of from 6 to 10, wherein the pH adjusting agent is at least one of sodium hydroxide, potassium hydroxide, citric acid, and hydrochloric acid.

Embodiment 15: The formulation of Embodiment 14, wherein the formulation comprises from 1% w/v to 5% of the flavorant and wherein the flavorant is lemon and lime.

Embodiment 16: The formulation of Embodiment 14 or 15, wherein the formulation comprises a pH adjusting agent that is citric acid.

Embodiment 17: The formulation of any one of Embodiments 14 to 16, wherein the solvent is glycerin.

Embodiment 18: The formulation of any one of Embodiments 14 to 17, wherein the carbonate is sodium carbonate.

Embodiment 19: The formulation of any one of Embodiments 14 to 18, wherein the formulation further comprises from 0.1% w/v to 2.5% w/v of one or more of EDTA, EGTA, and EDDS.

Embodiment 20: A liquid pharmaceutical formulation, suitable for oral administration, that comprises:

about 40 mg/ml of hydroxychloroquine sulfate;
about 0.035% w/v of sodium carbonate;
about 1235 mg/ml of glycerin;
about 1% w/v of an EDTA;
about 4% w/v of a sweetener that is sucralose.
about 2% w/v of a flavorant that is a mixture of lemon and lime; and
an amount of citric acid sufficient to adjust the pH of the formulation to from about pH 6 to about pH 10.

EXAMPLES

Aspects of embodiments of the present disclosure may be further understood in light of the following examples, which should not be construed as limiting in any way. Objectives of the oxidative degradation experiments of the present disclosure were to discover the resistance to degradation of hydroxychloroquine (HCQ), or a pharmaceutically acceptable salt thereof (e.g., HCQ sulfate), in a variety of liquid formulations. The HCQ studied was HCQ sulfate.

Example 1

Liquid HCQ formulations and hydrogen peroxide mediated oxidative degradation experiments. Liquid HCQ formulations 266-20A, 266-20B, 266-20C, and 266-20D comprised the ingredients set forth in Table 1.1 and were studied in the oxidative degradation experiments and samples analyzed in the HCQ and related substances assay described in this Example 1.

TABLE 1.1

HCQ sulfate formulations 266-20A-D

| Ingredient | 266-20A mg/25 ml | 266-20B mg/25 ml | 266-20C mg/25 ml | 266-20D (control) mg/25 ml |
|---|---|---|---|---|
| Hydroxychloroquine sulfate | 1,000 | 1,000 | 1,000 | 1,000 |
| Glycerin | 30,870 | 30,870 | 30,870 | 0 |
| Sodium citrate | 1,200 | 1,200 | 1,200 | 0 |
| Citric acid | 625 | 625 | 625 | 0 |
| Sucralose | 1,000 | 1,000 | 1,000 | 0 |
| Sodium carbonate | 0 | 0 | 8.75 | 0 |
| Lemon/lime flavor | 500 | 500 | 500 | 0 |
| EDTA | 0 | 250 | 250 | 0 |
| Sodium chloride | 0 | 0 | 0 | 500 |
| Sodium methylparaben | 0 | 0 | 0 | 37.5 |
| Purified water | 0 | 500 | 500 | 20,000 |

Liquid HCQ formulations. Formulations 266-20A, 266-20B, 266-20C, and 266-20D were made as follows. The amounts of ingredients listed in Table 1.1 for each formulation were weighed and transferred into one 25-ml volumetric flask for each formulation. The indicated diluent was then added to each flask to achieve the final 25 ml volume. The resultant formulations were mixed with a magnetic stir bar until a homogeneous solution was achieved. The solutions were then heated to 50° ° C. under continued stirring. 1.5 ml of each formulation were transferred to two microcentrifuge tubes, one of which was centrifuged at 5000 rpm for 2 minutes at room temperature and the other of which was kept as control (no centrifugation). The supernatant of the centrifuged tube was transferred to a fresh microcentrifuge tube. For each formulation, samples of the uncentrifuged formulation and the supernatant were analyzed in the HCQ Assay and related substances assay as described below.

Hydrogen peroxide mediated oxidative degradation experiments. To 5 ml aliquots of each of formulations 266-20A, 266-20B, 266-20C, and 266-20D, 375 ul of 3% v/v hydrogen peroxide was added and placed in oven at 60° C. for 1 day and 7 days and then analyzed for HCQ by the HCQ assay and related substances (RS) assay described below.

HCQ and related substances assays. The reference standards, reagents, and solutions used in the HCQ assay and related substances analytical methods of the present disclosure were as set forth in Table 1.2.

TABLE 1.2

HCQ assay and related substance assay reference standards, reagents, and solutions

| | |
|---|---|
| HCQ sulfate USP | Reference standard or secondary reference standard. |
| HCQ-N-oxide | Standard. |
| Acetonitrile | HPLC grade. |
| Potassium dihydrogen orthophosphate | Analytical reagent grade. |
| Orthophosphoric acid | Analytical reagent grade. |
| Water | Purified water. |
| Buffer solution | 6.8 g of potassium dihydrogen orthophosphate was weighed and transferred into a 1000 ml volumetric flask and diluted to volume with purified water. The resultant solution was adjusted to pH 2.4 with orthophosphoric acid. |
| Mobile Phase A | A degassed mixture of buffer solution and acetonitrile (95:5 v/v) was prepared. |
| Mobile Phase B | A degassed mixture of buffer solution and acetonitrile (30:70 v/v) was prepared. |
| Diluent | Same as mobile phase A. |
| Resolution stock solution | 2 mg of HCQ-N-oxide standard was weighed and transferred into a 200 ml volumetric flask, 160 ml of diluent was added, and the resultant solution was sonicated until the HCQ-N-oxides was dissolved and then diluted to 200 ml with diluent and mixed well |
| Resolution solution | 20.0 mg of HCQ sulfate standard was weighted and transferred into a 200 ml volumetric flask and then 160 ml of diluent was added. The resultant solution was sonicated until the HCQ was dissolved, then 3.0 ml of resolution stock solution was added and diluted to 200 ml with the diluent and mixed well. The HCQ Sulfate concentration was 0.1 mg/ml and the HCQ-N-oxide concentration was 15 μg/ml of the diluent. |

TABLE 1.2-continued

HCQ assay and related substance assay reference standards, reagents, and solutions

| | |
|---|---|
| Standard stock solution | 50.0 mg of HCQ sulfate standard was weighted and transferred into a 50 ml volumetric flask and 30 ml of diluent was added. The resultant solution was sonicated until dissolved and then diluted to 50 ml with diluent and mixed well. |
| Standard solution | 10.0 ml of standard stock solution was transferred into a 100 ml volumetric flask, diluted to 10 ml, and mixed well. The HCQ sulfate concentration was 0.1 mg/ml. |
| Standard check stock solution | Prepared the same as standard stock solution. |
| Standard check solution | 10.0 ml of standard check stock solution was transferred into a 100 ml volumetric flask, diluted to 100 ml, and mixed well. The HCQ sulfate concentration was 0.1 mg/ml. |
| Sensitivity solution | 1.0 ml of standard solution was transferred into a 10 ml volumetric flask and diluted to 10 ml with diluent and then mixed well. 1.0 ml of the resultant solution was transferred into a 100 ml volumetric flask, diluted to 100 ml with diluent and mixed well. The HCQ sulfate concentration was 0.1 µg/ml |
| Sample Solution (In-process and Finished product) | Based on the target concentration of the sample, serial dilution in diluent were prepared to achieve solutions that contained about 0.05 mg to 0.15 mg HCQ sulfate. |

The high-performance liquid chromatography ("HPLC") conditions for the HCQ assay and related substances assay employed in the present disclosure were according to those set forth in Table 1.3.

TABLE 1.3

HCQ assay and related substances HPLC parameters

| Chromatographic parameters | Equipment and/or conditions |
|---|---|
| System | HPLC system equipped with, Binary gradient and UV detector |
| Column | YMC pack Pro C18, (250 × 4.6) mm, 5 µm |
| Column Temperature | 40° C. ± 2° C. |
| Sample Tray Temperature | 25° C. |
| Detector Wavelength | UV 220 nm |
| Pump Mode | Gradient |
| Flow Rate | 1.7 ml/min |
| Injection Volume | 20 µl |
| HCQ sulfate retention time | Between 6.0 and 8.5 minutes |
| Run Time | 45 minutes |

The HPLC gradient elution program used in the HCQ and related substances HPLC assay was as set forth in Table 1.4.

TABLE 1.4

HPLC gradient elution program for HCQ assay and related substances

| Time in (Min) | Mobile phase A (% v/v) | Mobile phase B (% v/v) |
|---|---|---|
| 0 | 93 | 7 |
| 10 | 93 | 7 |
| 25 | 65 | 35 |
| 35 | 65 | 35 |
| 37 | 93 | 7 |
| 45 | 93 | 7 |

HPLC steps. Step 1. The HPLC system was equilibrated with mobile phase A for about 30 minutes. Iterative injections of diluent were made until a clean and reproducible baseline was achieved. The chromatogram was recorded and used to identify any peak eluting at the retention time of major peaks. Step 2. One injection of sensitivity solution into the HPLC column was performed. The chromatogram was recorded and used to identify the HCQ peak and calculate its signal to noise ratio. Step 3. One injection of resolution solution into the HPLC column was performed. The chromatogram was recorded and used to identify HCQ and HCQ-n-oxide peaks and the resolution between those peaks was calculated. Step 4. Six replicate injections of standard solution into the HPLC column were performed. The chromatograms were recorded and used to calculate the average and % RSD for the HCQ peak area responses obtained from the six replicate injections of standard solution. The tailing factor was determined. Step 5. Two replicate injections of standard check solution into the HPLC column were performed. The chromatograms were recorded and used to calculate average peak area responses of the HCQ obtained from the two replicate injections of standard check solution. The similarity factor was calculated. Step 6. One injection of diluent into the HPLC column was performed before injecting sample solutions. Step 7. One injection of sample solution into the HPLC column was made for six independent samples. The chromatograms for each of the six injected samples were recorded and used to determine the peak area of HCQ. The HCQ concentration in the sample solution was calculated. Steps 8 and 10. After every six injections of sample solution and at the end of the sequence, one injection of diluent into the HPLC column was performed. Step 9. One injection of standard solution into the HPLC column was made (bracketing) after every six injections. The chromatogram was recorded and used to determine peak area of HCQ in standard solution (bracketing). The % RSD was calculated of HCQ peak area obtained from the initial 6 injections of standard solution and bracketing standard.

The equation employed to calculate the similarity factor in the HCQ and related substances assay were as set forth in Table 1.5.

TABLE 1.5

HCQ assay and related substances assay similarity factor equation $$\text{Similarity factor} = \frac{Acstd}{Awstd} \times \frac{Wwstd}{Wcstd} \times 100$$

Where:

Acstd = peak area of the check standard
Awstd = peak area of the working standard
Wwstd = weight of the working standard
Wcstd = weight of the check standard The equations employed to calculate the % assay, assay in mg/ml (formulation), and % known and unknown impurities in the HCQ and related substances assay were as set forth in Table 1.6.

TABLE 1.6

HCQ Assay (in % and in mg/mL formulation) and Related Substances (% known and unknown impurities) Calculations $$\% \text{ Assay} = \frac{Aspl}{Astd} \times \frac{Wstd}{50 \text{ mL}} \times \frac{P}{100\%} \times \frac{10 \text{ mL}}{100 \text{ mL}} \times \frac{Wspl}{50 \text{ mL}} \times \frac{100 \text{ mL}}{10 \text{ mL}} \times 100\%$$

$$\text{Assay (mg/mL)} = \frac{Aspl}{Astd} \times \frac{Wstd}{50 \text{ mL}} \times \frac{P}{100\%} \times \frac{10 \text{ mL}}{100 \text{ mL}} \times \frac{V1spl}{VD1} \times \frac{V2spl}{VD2} \times 100\%$$

$$\% \text{ Impurity} = \frac{Aimp}{Astd} \times \frac{Wstd}{50 \text{ mL}} \times \frac{P}{100\%} \times \frac{10 \text{ mL}}{100 \text{ mL}} \times \frac{Wspl}{50 \text{ mL}} \times \frac{100 \text{ mL}}{10 \text{ mL}} \times CF \times 100\%$$

Where:
A spl = Peak area of Hydroxychloroquine obtained from the sample solution
A imp = Peak area of Individual impurity obtained from the sample solution
Astd = Peak area of the Hydroxychloroquine Sulfate obtained from standard solution
Wstd = Weight of Reference standard used to prepare standard solution
Wspl = Weight of API used to prepare sample solution
P = Potency/assay of Hydroxychloroquine Sulfate standard in percentage (on as is basis)
VD1spl = Volume of formulation sample used for first dilution
V1spl = Volume of volumetric flask used for first dilution
VD2spl = Volume of first dilution used for second dilution
V2spl = Volume of volumetric flask used for second dilution
CF = correction factor of respective impurity The relative retention time (RRT) and correction factor (CF) of impurities in the HCQ and related substances assay were as set forth in Table 1.7.

TABLE 1.7

RRT and CF of impurities in the HCQ and related substances assay

| Impurity | RRT | CF |
|---|---|---|
| Desethyl Hydroxychloroquine | 0.84 | 0.77 |
| Hydroxychloroquine-N-oxide | 1.30 | 0.89 |
| Hydroxychloroquine-O-acetate | 1.61 | 0.89 |
| Hydroxychloroquine-O-sulfate | 1.99 | 1.05 |
| Any unspecified impurity | Report | 1.00 |

Limit of quantification (LOQ) values of HCQ sulfate and known impurities in the HCQ assay and related substances assay were as set forth in Table 1.8.

TABLE 1.8

LOQ values of HCQ sulfate and known impurities in the HCQ assay and related substances

| Components | LOQ (%) |
|---|---|
| Hydroxychloroquine Sulfate | 0.03 |
| Desethyl Hydroxychloroquine | 0.02 |

TABLE 1.8-continued

LOQ values of HCQ sulfate and known impurities in the HCQ assay and related substances

| Components | LOQ (%) |
|---|---|
| Hydroxychloroquine-N-oxide | 0.03 |
| Hydroxychloroquine-O-acetate | 0.03 |
| Hydroxychloroquine-O-sulfate | 0.04 |

The results of the HCQ assay analysis of the oxidative degradation experiments conducted on the 266-20A, 266-20B, 266-20C, and 266-20D formulations are reported in Table 1.9.1 and Table 1.9.2.

TABLE 1.91

HCQ assay results in percent (%) for oxidative degradation experiments

| | 266-20A | | | 266-20B | | |
|---|---|---|---|---|---|---|
| | Initial | 60° C. Day 1 | 60° C. Day 7 | Initial | 60° C. Day 1 | 60° C. Day 7 |
| HCQ assay | 94.26 | 83.59 | 22.15 | 92.72 | 101.00 | 31.55 |
| HCQ assay drop | NA | −10.67 | −72.11 | NA | 8.28 | −61.17 |
| Desethyl HCQ | ND | 0.04 | 0.04 | ND | 0.04 | 0.04 |

TABLE 1.91-continued

HCQ assay results in percent (%)
for oxidative degradation experiments

|  | 266-20A | | | 266-20B | | |
| --- | --- | --- | --- | --- | --- | --- |
|  | Initial | 60° C. Day 1 | 60° C. Day 7 | Initial | 60° C. Day 1 | 60° C. Day 7 |
| HCQ N-oxide | ND | 5.35 | 56.79 | ND | 0.23 | 50.67 |
| Total impurities | 0.00 | 5.45 | 57.44 | 0.00 | 0.38 | 51.36 |

ND = not detected

TABLE 1.9.2

HCQ assay results in percent (%)
for oxidative degradation experiments

|  | 266-20C | | | 266-20D | | |
| --- | --- | --- | --- | --- | --- | --- |
|  | Initial | 60° C. Day 1 | 60° C. Day 7 | Initial | 60° C. Day 1 | 60° C. Day 7 |
| HCQ assay | 95.03 | 99.48 | 83.76 | 95.00 | 88.42 | 59.06 |
| HCQ assay drop | NA | 4.45 | −11.27 | NA | −6.58 | −35.94 |
| Desethyl HCQ | ND | 0.05 | 0.10 | ND | 0.07 | 0.05 |
| HCQ N-oxide | ND | 0.05 | 0.44 | ND | 0.21 | 15.54 |
| Total impurities | 0.00 | 0.17 | 1.50 | 0.00 | 2.70 | 16.83 |

ND = not detected

While the foregoing specification teaches the principles of the present invention, with examples provided for the purpose of illustration, it will be understood that the practice of the invention encompasses all variations, adaptations and/or modifications as come within the scope of the following claims and their equivalents.

What is claimed is:

1. A liquid pharmaceutical formulation, suitable for oral administration, comprising:
   from 30 mg/ml to 50 mg/ml hydroxychloroquine (HCQ);
   from 1,000 mg/ml to 1,250 mg/ml glycerin;
   from 0.2 mg/ml to 0.5 mg/ml a carbonate that is at least one of a sodium carbonate, potassium carbonate, calcium carbonate, magnesium carbonate, ammonium carbonate, sodium bicarbonate, potassium bicarbonate, calcium bicarbonate, magnesium bicarbonate, and ammonium bicarbonate;
   from 1 mg/ml to 25 mg/ml ethylenediaminetetraacetic acid (EDTA);
   an amount of citric acid sufficient to yield a pH of the formulation of from 6 to 10; and
   ≤20 mg/ml water,
   wherein the formulation exhibits an assay drop of from about 5% to about 20% at day 7 at 60° C. in the oxidative degradation experiment described in Example 1.

2. The formulation of claim 1, wherein the assay drop is from about 10% to about 20%.

3. The formulation of claim 1, wherein the assay drop is from about 10% to about 15%.

4. The formulation of claim 1, wherein the carbonate is sodium carbonate.

5. The formulation of claim 4, wherein the assay drop is from about 10% to about 20%.

6. The formulation of claim 4, wherein the assay drop is from about 10% to about 15%.

7. A liquid pharmaceutical formulation, suitable for oral administration, that comprises:
   about 40 mg/ml hydroxychloroquine sulfate;
   about 0.35 mg/ml sodium carbonate;
   about 1,235 mg/ml glycerin;
   about 10 mg/ml EDTA;
   about amount of citric acid sufficient to adjust the pH of the formulation to from about pH 6 to about pH 10; and
   ≤20 mg/ml water.

* * * * *